United States Patent
Lee

(10) Patent No.: US 6,277,093 B1
(45) Date of Patent: *Aug. 21, 2001

(54) LUBRICIOUS AND READILY BONDABLE CATHETER SHAFT

(75) Inventor: Jeong Soo Lee, Diamond Bar, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/976,447

(22) Filed: Nov. 25, 1997

Related U.S. Application Data

(63) Continuation of application No. 08/587,330, filed on Jan. 16, 1996, now abandoned.

(51) Int. Cl.[7] .................................................. A61M 29/00
(52) U.S. Cl. .............................. 604/96; 604/523; 606/194
(58) Field of Search .............................. 604/96, 282, 265, 604/264, 93, 104, 266, 172, 523, 524; 606/194

(56) References Cited

U.S. PATENT DOCUMENTS

| | | | |
|---|---|---|---|
| 3,458,596 | 7/1969 | Faigle et al. | 260/867 |
| 4,616,064 | * 10/1986 | Zukosky et al. | 525/92 |
| 4,945,126 | 7/1990 | Crosby et al. | 524/507 |
| 4,955,895 | * 9/1990 | Sugiyama et al. | 606/194 |
| 5,267,959 | * 12/1993 | Forman | 604/103 |
| 5,304,134 | 4/1994 | Kraus et al. | 604/96 |
| 5,348,538 | * 9/1994 | Wang et al. | 604/96 |
| 5,443,907 | * 8/1995 | Slaikeu et al. | 428/375 |
| 5,503,631 | * 4/1996 | Onishi et al. | 604/96 |
| 5,549,552 | * 8/1996 | Peters et al. | 604/96 |
| 5,554,120 | * 9/1996 | Chen et al. | 604/96 |
| 5,556,383 | * 9/1996 | Wang et al. | 604/96 |
| 5,868,706 | * 2/1999 | Cox | 604/96 |

FOREIGN PATENT DOCUMENTS

| | | |
|---|---|---|
| 0 124 955 A1 | 11/1984 | (EP) . |
| WO 92/08512 | 5/1992 | (WO) . |
| WO93/15781 | 8/1993 | (WO) . |
| WO 94/00176 | 1/1994 | (WO) . |
| WO 95/09667 | 4/1995 | (WO) . |
| WO 96/03163 | 2/1996 | (WO) . |
| 0747 070 A2 | 12/1996 | (WO) . |

* cited by examiner

*Primary Examiner*—Corrine McDermott
*Assistant Examiner*—Cris L. Rodriguez
(74) *Attorney, Agent, or Firm*—Heller Ehrman White & McAuliffe

(57) ABSTRACT

An intraluminal catheter, particularly a dilatation catheter for angioplasty procedures, which has a shaft section formed of a blend of lubricous and bonding polymeric components in proportions to maintain a low coefficient of friction while maintaining the ability to bond non-lubricous polymeric material, e.g. polyethylene terephthalate, to the segment.

15 Claims, 3 Drawing Sheets

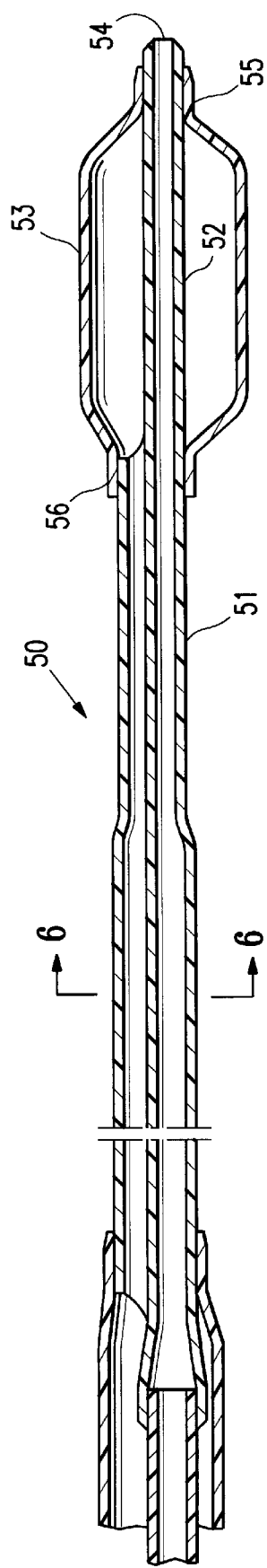
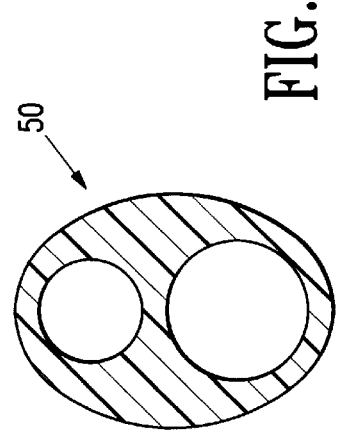
FIG. 5
FIG. 6

LUBRICIOUS AND READILY BONDABLE CATHETER SHAFT

This is a continuation of application Ser. No. 08/587,330, which was filed on Jan. 16, 1996, now abandoned.

BACKGROUND OF THE INVENTION

This invention relates to catheters for performing intravascular procedures such as percutaneous transluminal coronary angioplasty (PTCA) and more specifically to elongated shafts for such catheters.

PTCA is now one of the most widely used treatment modalities for heart disease. The procedure basically comprises advancing a dilatation catheter, having an inflatable balloon on its distal extremity, into the patient's coronary anatomy over a guidewire until the balloon of the dilatation catheter is properly positioned across the lesion to be dilated. Once properly positioned, the dilatation balloon is inflated with liquid to a predetermined size at relatively high pressures, e.g. up to 20 atmospheres or more, to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In most PTCA procedures, a guiding catheter having a preshaped distal tip is first percutaneously introduced into the cardiovascular system of a patient by means of a conventional Seldinger technique and advanced therein until the preshaped distal tip of the guiding catheter is disposed within the aorta adjacent to the ostium of the desired coronary artery. The guiding catheter is twisted or torqued from its proximal end, which extends out of the patient, to guide the distal tip of the guiding catheter into the desired coronary ostium. Once the guiding catheter is in proper position within the patient's vasculature, the dilatation catheter with a guidewire slidably disposed within an inner lumen of the dilatation catheter is positioned within the inner lumen of the guiding catheter. The guidewire is first advanced out the distal tip of the guiding catheter seated in the coronary ostium into the patient's coronary artery and directed to the region of the patient's coronary anatomy where the procedure is to occur. A torque may be applied to the proximal end of the guidewire, which extends out of the proximal end of the guiding catheter, to guide the curved or otherwise shaped distal end of the guidewire into a desired branch of the coronary artery. The advancement of the guidewire within the selected artery continues until it crosses the lesion to be dilated. The dilatation catheter is then advanced over the previously advanced guidewire, until the balloon on the distal extremity of the dilatation catheter is properly positioned across the lesion which is to be dilated.

Current intravascular catheter designs are limited by the need to incorporate conflicting characteristics. For example, most dilatation catheters are designed to be introduced into a body lumen over an in-place guidewire which is slidably received within an inner lumen within the catheter. As such, it is desirable to minimize the friction between the guidewire and the surface of the inner lumen of the catheter by constructing the catheter from a lubricous material such as a high density polyethylene. However, lubricous polymeric materials frequently lack other desirable properties, including, for example, the ability to readily bond to incompatible polymeric materials such as polyethylene terephthalate and nylon. Due to the high inflation pressures (up to 300 psi or more) associated with coronary balloon angioplasty, it is imperative to provide a strong bond between one or more ends of the dilatation balloon and the catheter shaft. Polyolefin balloons can be effectively fusion bonded to a polyethylene shaft but balloons made of nylon and other polyamide materials, and balloons made of polyesters such as polyethylene terephthalate do not easily bond to polyolefinic materials. Nylon and polyethylene terephthalate balloons usually require surface treatment and the use of a suitable adhesive to bond to polyolefin materials such as polyethylene. The additional manufacturing steps of surface treatments and incorporating and curing an adhesives, greatly complicate the manufacturing process and can introduce significant quality control problems. A catheter shaft should also have adequate strength for pushability and resistance to buckling or kinking. As another example, it may be desirable to provide a catheter shaft with elastomeric properties to improve flexibility. However, most lubricous materials are not elastomeric.

U.S. Pat. No. 5,304,134 to Kraus et al., which is hereby incorporated in its entirety by reference, attempts to provide a solution to the poor bonding of lubricous by providing the catheter shaft with an inner tubular member having a lubricous proximal portion and a non-lubricous, bondable distal portion. However, this approach does not represent a complete solution, because the lubricous proximal portion must still be bonded to the non-lubricous distal portion. The Kraus et al. system also requires that some portion of the guidewire lumen be formed from a non-lubricous material which restricts guidewire movement within the lumen.

A different approach involves forming the dilatation balloon as an integral portion of the catheter shaft itself, but this requires the balloon and the shaft to be formed from the same material, which is not always desirable because the property requirements for the balloon and the shaft can be quite different, particularly for dilatation catheters for PTCA.

Accordingly, there remains a need to provide a catheter shaft having a lubricous inner surface defining a guidewire lumen while allowing an easy, secure bond with a dilatation balloon or other catheter components formed of non-lubricous polymeric materials. The present invention satisfies these and other needs.

SUMMARY OF THE INVENTION

The present invention is directed to an intraluminal catheter, such as a balloon dilatation catheter for performing angioplasty procedures, which has a shaft or shaft segment which is both lubricous and is capable of readily bonding to other catheter components such as a balloon formed of essentially non-lubricous polymers.

In accordance with the present invention, the catheter shaft or catheter shaft segment is formed of a polymeric blend comprising at least about 30% by weight, preferably at least about 50% by weight of a lubricous polymeric component, not more than about 60%, preferably not more than about 40% of a bonding polymeric component and up to about 30%, preferably not more than about 10% of a polymeric component for compatiblizing the lubricous and bonding components. Optionally, up to 25% by weight, usually not more than about 10% by weight of the blend should be a catalytic material to facilitate cross linking the shaft material after forming the product. The lubricous component and the bonding component must be compatible or capable of being made compatible. As used herein the term "compatible" and words of similar import mean that two polymer materials readily form an intimate mixture when they are melt processed together. Usually, they are miscible when both are in a molten condition.

In one presently preferred embodiment, the catheter or catheter segment is formed of a blend of about 50% to about 80% polyethylene (a lubricous component), about up to about 50% of a copolyester such as Hytrel® (the bonding component) and up to about 50% of a compatiblizing agent such as an acrylate. The polymer components are intimately mixed and extruded into a tubular product which is utilized as the inner tubular member of an intravascular catheter. The surface defining an inner lumen of the tubular member has a kinematic frictional coefficient of about 0.08 to about 0.3 on a smooth glass. A balloon formed of PET readily fusion bonds to the outer surface of the tubular member.

These and other advantages of the invention will become more apparent from the following detailed description of the invention when taken in conjunction with the accompanying exemplary drawings.

BRIEF DESCRIPTION OF THE DRAWINGS

FIG. 5 is an elevational view, partially in section, of an alternative embodiment wherein the distal section of the catheter shaft is formed of an extrusion of a polymer blend.

FIG. 6 is a transverse cross section of the embodiment shown in FIG. 5 taken along the lines 6—6.

DETAILED DESCRIPTION OF THE INVENTION

Figure 1:
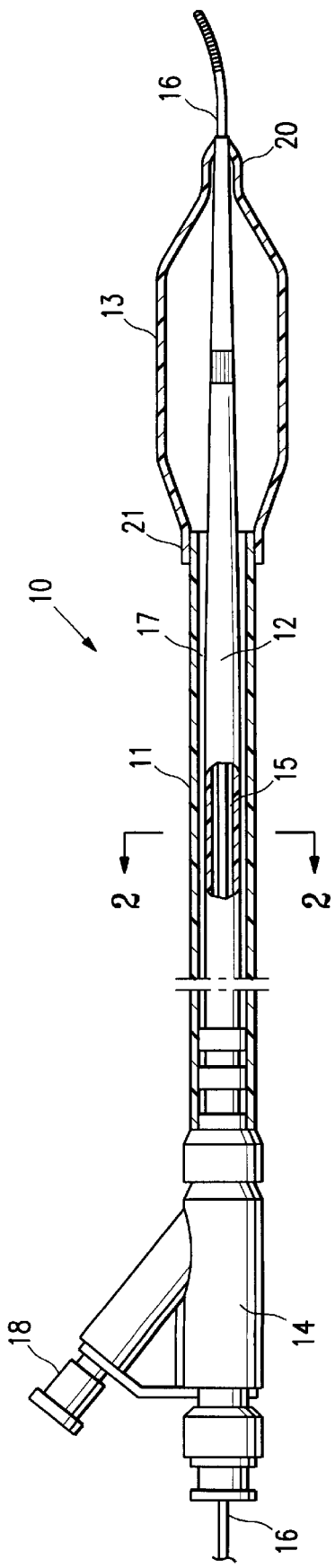
FIG. 1 is an elevational view, partially in section, of an over-the-wire dilatation catheter having an inner tubular member embodying features of the invention.
Figure 2:
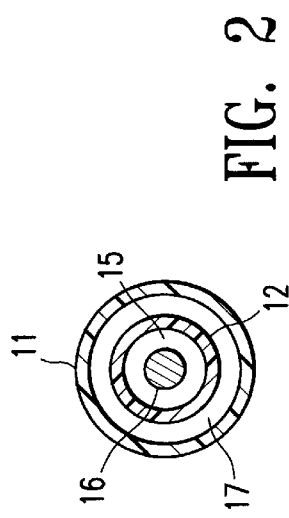
FIG. 2 is a transverse cross section of the embodiment shown in FIG. 1 taken along the lines 2—2.

Reference is made to FIGS. 1 and 2 which illustrate a balloon dilatation catheter 10 embodying features of the invention. Generally, the catheter 10 comprises an outer tubular member 11, an inner tubular member 12, a dilatation balloon 13 on a distal portion of the catheter and an adapter 14 on the proximal end of the catheter. The inner tubular member 12 has a guidewire receiving inner lumen 15 which slidably receives guidewire 16. The outer surface of the inner tubular member 12 and the inner surface of the outer tubular member 11 define an annular inflation lumen 17 which is in fluid communication with the interior of balloon 13 and side arm 18 of adapter 14.

The distal skirt 20 of balloon 13 is bonded, preferably fusion bonded, to the exterior of the inner tubular member 12 and the proximal skirt 21 is fusion bonded to the exterior of the outer tubular member 11.

The fusion bonds are preferably formed by applying laser energy to the exterior of the skirts 20 and 21 which causes the interface between the skirts and the exterior of the outer and inner tubular members 11 and 12.

In one presently preferred embodiment, both the outer and inner tubular members 11 and 12 are formed of a polymer blend in accordance with the invention having a lubricous polymeric component and a bonding polymeric component.

Figure 3:
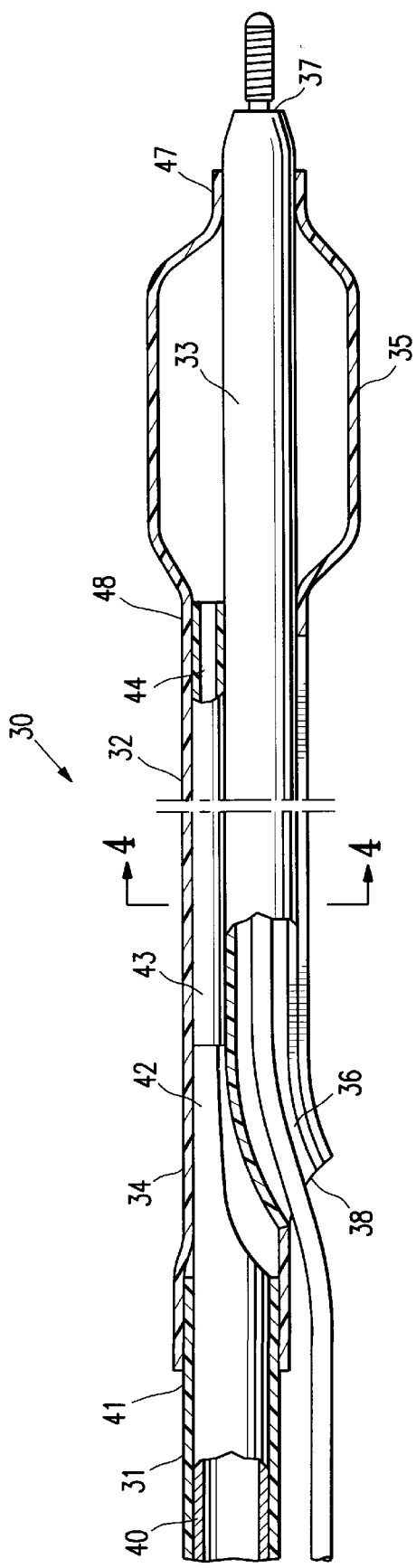
FIG. 3 is an elevational view, partially in section, of the distal section of a rapid exchange type dilatation catheter having an inner tubular member embodying features of the invention.
Figure 4:
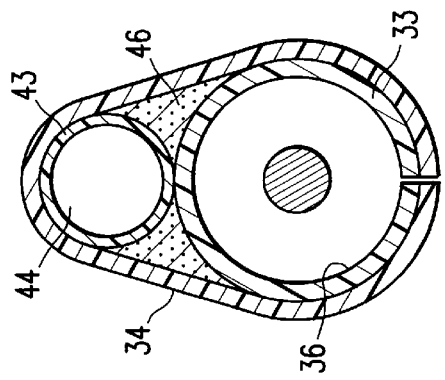
FIG. 4 is a transverse cross section of the embodiment shown in FIG. 3 taken along the lines 4—4.

FIGS. 3–4 depict another embodiment of the invention directed to a rapid exchange type dilatation catheter 30. The catheter 30 includes a relatively stiff proximal shaft 31 formed of hypotubing and a relatively flexible distal shaft section 32. The distal shaft section 32 includes an inner tubular member 33, an outer tubular member 34 and a dilation balloon 35. The inner tubular member 33 has a guidewire receiving inner lumen 36 which is in fluid communication with a distal guidewire port 37 in the distal end of the catheter 30 and a proximal guidewire port 38 disposed a short distance, e.g. about 10 to about 45 cm from the proximal end of the balloon 35. The proximal shaft 31 comprises a metallic hypotube 40 (e.g. stainless steel or NiTi alloys) and an outer polymer jacket 41 formed of suitable polymer material such as high density polyethylene. The distal end 42 of the hypotube 40 is truncated and fits into the interior of the outer tubular member 34 and bonded thereto by suitable adhesive (not shown). Support tube 43, preferably formed of polyimide, is disposed between the inner and outer tubular members 33 and 34 and defines inflation lumen 44. As shown in more detail in FIG. 4, the outer tubular member is partially bonded to the inner tubular member 33 and partially to the support tube 43. A filler material 46, such as 75/25 high density/low density polyethylene, is disposed between the outer tubular member 34 and the support tube 43.

In the embodiment of FIGS. 3–4 the inner tubular member 33 is formed of a polymer blend in accordance with the present invention. The distal skirt 47 of balloon 35 is fusion bonded to the exterior of the inner tubular member 33 as in the previously discussed embodiment shown in FIGS. 1 and 2. The proximal skirt 48 of the balloon 35 forms the outer tubular member 34 and is formed of essentially the same material as the balloon. In an alternative embodiment not shown the outer tubular member 34 may be a member separate and distinct from the balloon and formed of a polymer blend in accordance with the present invention. In this latter case the proximal skirt of the balloon 35 is fusion bonded to the exterior of the outer tubular member.

FIGS. 5 and 6 illustrate yet another embodiment of the invention wherein the catheter 50 has a distal shaft 51 which is of a dual lumen construction and is formed by extruding a polymer blend in accordance with the present invention. A tubular extension 52 extends through the interior of the dilatation balloon 53 and has a distal guidewire port 54 in its distal end. The balloon 53 has a distal skirt 55 fusion bonded to the distal end of the tubular extension 52 and a proximal skirt 56 fusion bonded to the distal shaft 51 as shown in the drawings.

A presently preferred polymer blend includes about 65% high density polyethylene, about 30% Hytrel® (available from Dupont) and about 5% ethylene methyl acrylate such as Lotryl 24MA005 (available from Elf ATOCHEM). This blend readily fusion bonds to polyethylene terephthalate and has a coefficient of friction of about 0.1–0.2.

Although individual features of embodiments of the invention may be shown in some of the drawings and not in others, those skilled in the art will recognize that individual features of one embodiment of the invention can be combined with any or all the features of another embodiment. A variety of modifications can be made to the present invention without departing from the scope thereof.

What is claimed is:

1. An intraluminal catheter having an elongated shaft which has proximal and distal portions and which has at least a lubricious catheter shaft segment thereof fusion bonded to another catheter element, wherein the lubricious catheter shaft segment is formed of a polymeric blend having a lubricious high density polymeric component and a bonding polymeric component, and the catheter element is formed of a non-lubricious polymeric material.

2. The intraluminal catheter of claim 1 wherein the catheter element is a balloon.

3. The intraluminal catheter of claim 1 wherein the bonding polymeric component is compatiblized with the lubricious high density polymeric component by means of a compatiblizing agent.

4. The intraluminal catheter of claim 3 wherein the compatiblizing agent is a polymeric material formed at least in part of an acrylate monomer.

5. The intraluminal catheter of claim 3 wherein the compatiblizing agent is ethylene methyl acrylate.

6. The intraluminal catheter of claim 3 wherein the polymeric blend contains up to 50% of the compatibilizing agent.

7. The intraluminal catheter of claim 1 wherein the lubricious high density polymeric component is high density polyethylene.

8. The intraluminal catheter of claim 1 wherein the lubricious high density polymeric component comprises at least 30% by weight of the polymeric blend.

9. The intraluminal catheter of claim 1 wherein the lubricious high density polymeric component comprises at least 50% by weight of the blend.

10. The intraluminal catheter of claim 1 wherein the bonding polymeric component of the polymeric blend is a co-polyester material.

11. The intraluminal catheter of claim 1 wherein the polymeric blend includes a catalytic material to facilitate cross linking in the catheter shaft segment.

12. The intraluminal catheter of claim 1 wherein the lubricious high density polymeric component comprises about 50% to about 80% by weight of the polymeric blend.

13. A balloon dilatation catheter comprising:

a) an elongated shaft which has proximal and distal portions and which has at least a lubricious catheter shaft segment thereof fusion bonded to another catheter element, wherein the lubricious catheter shaft segment is formed of a polymeric blend having a lubricious high density polymeric component and a bonding polymeric component; and b) a dilatation balloon formed of non-lubricious material having at least a distal skirt fusion bonded to the catheter shaft segment.

14. The balloon dilatation catheter of claim 13 wherein the dilatation balloon is formed of polyethylene terephthalate.

15. An intraluminal catheter having an elongated shaft which has proximal and distal portions and which has at least a lubricious catheter shaft segment thereof fusion bonded to another catheter element, wherein the lubricious catheter shaft segment is formed of a polymeric blend having a lubricious high density polymeric component comprising at least 30% by weight of the polymeric blend and a bonding polymeric component.

* * * * *